(12) United States Patent
Usami et al.

(10) Patent No.: US 6,277,602 B1
(45) Date of Patent: *Aug. 21, 2001

(54) METHOD OF PRODUCING 1-MENTHYL-α-D-GLUCOPYRANOSIDE

(75) Inventors: Shoji Usami; Kohtaro Kirimura; Hiroyuki Nakagawa; Yukio Dobashi, all of Tokyo; Masaaki Yoshiyama, Gunma; Susumu Shimura; Yoshio Ito, both of Tokyo, all of (JP)

(73) Assignee: Lotte Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/201,156

(22) Filed: Nov. 30, 1998

(30) Foreign Application Priority Data

Nov. 29, 1997 (JP) .................................................. 9-343925

(51) Int. Cl.⁷ .................................................. C12P 19/46
(52) U.S. Cl. .............................. 435/79; 435/74; 435/170; 435/171; 435/193; 435/169
(58) Field of Search ................................. 435/74, 79, 170, 435/171, 193, 169

(56) References Cited

U.S. PATENT DOCUMENTS 5,455,168 * 10/1995 Maruta .................................. 435/201
5,770,405 * 6/1998 Wong-Madden et al. .............. 435/74

FOREIGN PATENT DOCUMENTS 8-238098 * 9/1996 (JP) .
9-224693 * 9/1996 (JP) .

OTHER PUBLICATIONS

Nakagawa, et al., Bioscience Biotechnology and Biochemistry, (Jul., 1998) vol. 62, No. 7, pp. 1332–1336.*
Noguchi, et al., Journal of Fermentation and Bioengineering, (1998) vol. 85, No. 4, pp. 436–438.*
Nakagawa, et al., Bioscience Biotechnology and Biochemistry, (1996) vol. 60, No. 11, pp. 1914–1915.*

* cited by examiner

Primary Examiner—Irene Marx
(74) Attorney, Agent, or Firm—Young & Thompson

(57) ABSTRACT

A method of producing 1-menthyl-α-D-glucopyranoside is provided, wherein microorganisms capable of producing 1-menthol glycoside from 1-menthol are added to sugars and 1-menthol. Bacteria selected from the group consisting of Xanthomonas species, Stenotrophomonas species and Arthrobacter species may be used as the microorganisms.

2 Claims, 9 Drawing Sheets spectrum of 13C-NMR analysis to 1-menthyl-α-D-glucopyranoside influence of reaction pH to production amount of menthol glycoside
● : phosphoric acid - citric acid buffer solution
○ : boric acid - NaOH buffer solution influence of reaction pH to production amount of menthol glycoside
● : phosphoric acid - citric acid buffer solution
○ : glycine - NaOH buffer solution influence of temperature to production amount of menthol glycoside
● : 50mg of menthol
▲ : 100mg of menthol influence of temperature to production amount of menthol glycoside influence of maltose concentration to production amount of menthol glycoside influence of maltose concentration to production amount of menthol glycoside influence of amount of menthol to production amount of menthol glycoside influence of reaction time to production amount of menthol glycoside

METHOD OF PRODUCING 1-MENTHYL-α-D-GLUCOPYRANOSIDE

BACKGROUND OF THE INVENTION

The present invention relates to a method of producing 1-menthyl-α-D-glucopyranoside.

Menthol has widely been used in pharmaceuticals, foods, tooth-pastes, other mouth refreshing and cooling agents due to such peppermint flavors providing unique mouth-refreshing and cooling functions. Menthol has a problem in decreasing peppermint flavors over time due to its sublimation property. Since menthol is also water-insoluble, in the prior art it is required that menthol in use is admixed in the form of solid particles or suspended with an emulsifier, or dissolved in an organic solvent such as alcohols.

In Japanese patent publication No. 51-105, it is disclosed that, in order to overcome the above problems, menthol glycoside is used, which has a bonding structure of menthol with oligosaccharide. This menthol glycoside is highly water-soluble and exhibits no peppermint flavor of menthol. Notwithstanding, menthol glycoside may be hydrolyzed with various kinds of carbohydrase or acids to be decomposed into menthol and sugars, whereby the peppermint flavor with refreshing and cooling feelings of menthol appears, which is disclosed in 1979 Agric. Biol. Chem. Vol. 43, p. 307 and also in 1981 "Essence" No. 130, 79.

Since menthol glycoside is water-soluble and has non-sublimation property, it is unnecessary to seal menthol glycoside from atmosphere for storage differently from menthol. Menthol glycoside is so highly stable as a chemical substance that menthol glycoside shows no chemical change even leaving the same alone without sealing. Further, menthol glycoside is easily controllable for displaying refreshing and cooling feelings of menthol and pharmaceutical functions by optimization or adjustment of decomposition rate so that menthol glycoside continuously or temporary displays the same.

Menthol glycoside is usable in various foods or as mouth-refreshing and cooling agents and tobacco's flavor improver and taste in order to act as a chemical stabilizer to continue the refreshing and cooling feelings In Japanese laid-open patent publication No. 62-161716, it is disclosed to apply menthol glycoside to toothpaste compositions. In Japanese laid-open patent publication No. 6-329528, it is disclosed to apply menthol glycoside to cosmetics to keep refreshing and cooling feelings for long time. In Japanese laid-open patent publication No. 5-219929, it is disclosed to apply menthol glycoside to tobaccos for improvement in flavor and taste.

Japanese patent publication No. 51-105 also discloses methods of producing menthol glycoside, for example, a method of organically synthesizing glucose with menthol to form menthyl-glycoside as well as an organic synthesis method using acetyl-glucose or acetopromo-glucose. In 1979 Agric. Biol. Chem. Vol 43, p. 307 and also in 1981 "Essence" No. 130, 79, there are disclosed a method of catabolism of menthyl-tetraacetyl β-glucopyranoside to synthesize menthyl-α-D-glucopyranoside or a method of organic synthesis of various kinds of menthol glycoside.

The above conventional methods utilize expensive catalysts and many reaction processes, resulting in high manufacturing costs. Further, in order to apply menthol glycoside to foods, it is required to completely remove organic synthesis reagent therefrom.

The present inventors had developed a conventional method of producing menthol glycoside without any expensive catalyst and many reaction processes to produce a highly safe product, wherein α-glucosidase is used to cause an enzyme reaction between a substrate of sugars such as sucrose and maltose and an acceptor of menthol, thereby to form menthol glycoside. This conventional method is disclosed in Japanese laid-open patent publication No. 9-224693. In accordance with this conventional method, menthol glycoside may be produced through a single reaction process without use of any organic synthesis reagent which is harmful for the human body or health. This conventional method is disadvantageous in too low yield to be practiced. If no surfactant is added, then the yield of produced menthol glycoside to used menthol is only about 5% in molar ratio. Even if a surfactant is added, then the yield is still low about 9%. Those yields are insufficient for practicing the above conventional method.

In the above circumstances, it had been required to develop a novel method of producing 1-menthyl-α-D-glucopyranoside as a menthol glycoside at high yield without use of any expensive catalyst and many reaction steps.

SUMMARY OF THE INVENTION

Accordingly, it is an object of the present invention to provide a novel method of producing a menthol glycoside free from the above problems.

It is a further object of the present invention to provide a novel method of producing 1-menthyl-α-D-glucopyranoside as a menthol glycoside at high yield without use of any expensive catalyst and many reaction steps.

The present invention provides a method of producing 1-menthyl-α-D-glucopyranoside, wherein microorganisms capable of producing 1-menthol glycoside from 1-menthol are activated in the presence of sugars and 1-menthol. Bacteria selected from the group consisting of Xanthomonas species, Stenotrophomonas species and Arthrobacter species may be used as the microorganisms.

The present invention also provides a method of producing 1-menthyl-α-D-glucopyranoside, wherein an enzyme prepared from microorganisms capable of producing 1-menthol glycoside from 1-menthol is activated in the presence of sugars and 1-menthol. Bacteria selected from the group consisting of Xanthomonas species, Stenotrophomonas species and Arthrobacter species is used as the microorganisms to prepare the enzyme.

The above and other objects, features and advantages of the present invention will be apparent from the following descriptions.

BRIEF DESCRIPTION OF THE DRAWINGS

Preferred examples according to the present invention will be described in detail with reference to the accompanying drawings.

DISCLOSURE OF THE INVENTION

Figure 1:
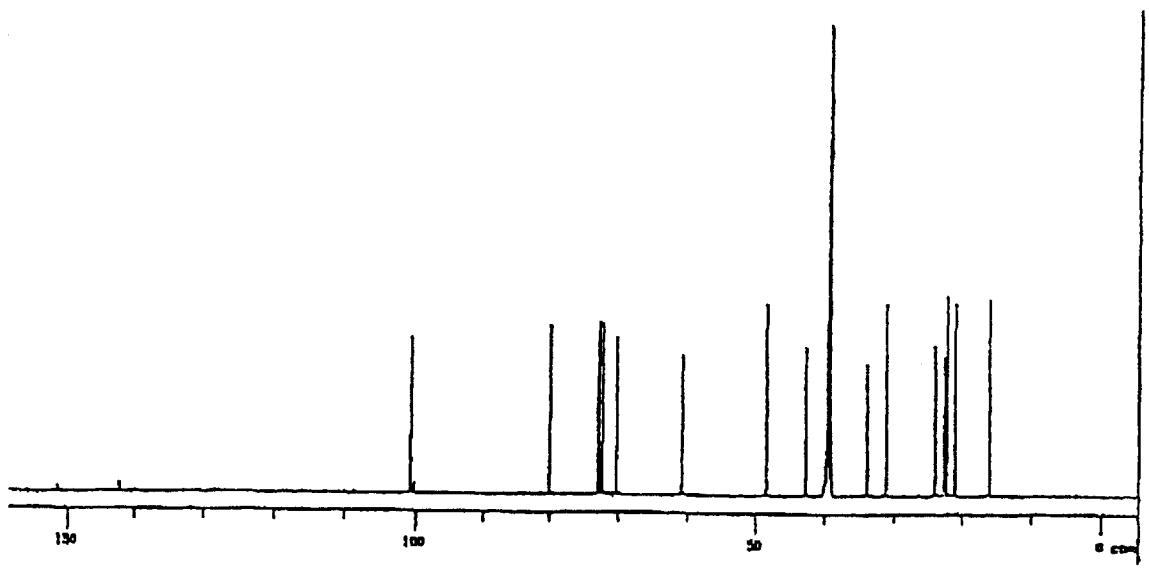
FIG. 1. is a diagram illustrative of spectrum of $^{13}$C-NMR analysis to 1-menthyl-α-D-glucopyranoside obtained by the method in accordance with the present invention.

The present invention provides a method of producing 1-menthyl-α-D-glucopyranoside, wherein microorganisms capable of producing 1-menthol glycoside from 1-menthol are activated in the presence of sugars and 1-menthol Bacteria selected from the group consisting of Xanthomonas species, Stenotrophomonas species and Arthrobacter species may be used as the microorganisms.

The present invention also provides a method of producing 1-menthyl-α-D-glucopyranoside, wherein an enzyme prepared from microorganisms capable of producing 1-menthol glycoside from 1-menthol is activated in the presence of sugars and 1-menthol. Bacteria selected from the group consisting of Xanthomonas species, Stenotrophomonas species and Arthrobacter species is used as the microorganisms to prepare the enzyme.

It was confirmed by the present inventors that bacteria of Xanthomonas species, Stenotrophomonas species or Arthrobacter species are capable of producing menthol glycoside from menthol at a much higher yield than when α-glucosidase is used. The method of producing menthol glycoside at high yield by utilizing microorganisms had not yet been known before the above facts have been confirmed by the present inventors.

Of Menthol, twelve kinds of isomers exist, wherein there exist four different kinds of stereoisomers, each of which is further classified into three different kinds of optical isomers. In accordance with the present invention, 1-menthol providing refreshing and cooling flavor is used as the kind of menthol. 1-menthol will hereinafter be referred to as menthol. Further, 1-menthyl-α-D-glucopyranoside will also hereinafter be referred to as menthol glycoside.

It is unnecessary to limit available microorganisms to the above species, provided that microorganisms are capable of producing menthol glycoside from menthol. It may easily be confirmed whether microorganisms are capable or incapable of producing menthol glycoside from menthol as follows. Menthol is added to a solution including sucrose, maltose, dextrin, or starch and then microorganisms or bacteria are added to the menthol-containing solution before a detection of glycoside is made by TLC or HPLC. If glycoside is detected, this means that microorganisms or bacteria are capable of producing menthol glycoside from menthol. If, however, no glycoside is detected, this means that microorganisms or bacteria are incapable of producing menthol glycoside from menthol. For example, Xanthomonas species, Stenotrophomonas species and Arthrobacter species are bacteria capable of producing menthol glycoside from menthol. Those bacteria are available from organizations for sale of strains, for example, Institute of Fermentation Research (Foundation) or Institute of Physical and Chemical Research (Foundation). *Xanthomonas campestris* WU9701 (FERM BP-6578) and *Stenotrophomonas maltophilia* D1 GERM BP-6579) as isolated and identified by the present inventors have high capabilities of producing menthol glycoside from menthol. Those microorganisms have been deposited under the above international deposition numbers in National Institute of Bioscience and Human-Technology in Agency of Industrial Science and Technology in Japan. Particularly, Xanthomonas species correspond to bacteria which are capable of producing viscosity improver polysaccharide xanthanegum used for producing foods. From a viewpoint of safety, it is more preferable to utilize Xanthomonas species.

Microorganisms may be used in various forms or states. For example, active bacteria, which have frozen dry bacteria, dead bacteria lost growth function with irradiation by ultraviolet rays, bacteria-crushed solutions are available. Further, immobilized bacteria obtained by immobilizing active bacteria onto a carrier such as an alginic acid, polyacrylamide, glass beads, and chitosan, crude enzymes prepared from bacteria-crushed solutions, and immobilized enzymes obtained by immobilizing crude enzymes onto a carrier are also available.

For synthesizing menthol glycoside, it is possible to add bacteria or crude enzymes into menthol-containing sugar solutions. It is also possible to cultivate bacteria on a medium usually used for microorganisms before menthol and sugars are added to that medium for cultivation of microorganisms and concurrent production of menthol glycoside from menthol. It is also possible to add little by little sugars to a mixing solution of menthol with microorganisms for continuously producing menthol glycoside from menthol.

Various sugars including glucose as a constitutive sugar are available for synthesizing menthol glycoside. For example, maltose, dextrin, soluble-starch and sucrose are available.

It is also possible to dissolve menthol in a solvent for causing the enzyme reaction. As organic solvent, hexane, ethyl acetate, ether, water-insoluble solvents such as oils and fats, and water-mixable solvents such as acetone and ethanol are usable alone or in combination. It is further optional to add surfactant.

Menthyl-glycoside as a reaction product may be separated and purified. It is also possible to use plain reaction solution or condensed reaction solution or possible to use dry reaction solution.

1-menthyl-α-D-glucopyranoside produced by the method of the present invention as well as an admixture containing the same may widely be used as safe and chemically stable menthols and also as foods and cosmetics material providing refreshing and cooling feelings of menthol upon gradual decomposition in mouth, as well as flavor for tobaccos, in addition, mothproof agents and antibacterial agents.

1-menthyl-α-D-glucopyranoside as a reaction product may be used as an acceptor to sugars to activate enzyme capable of causing transglycosidation for bonding a plurality of sugars to glucose residue of menthyl-glycoside to increase water-solubility and decomposition properties with acids, enzymes and heat. For example, 1-menthyl-α-D-glucopyranoside is used as the acceptor to sugars to activate cyclodextringlucanotransferase in the presence of dextrin or starch so that a plurality of glucose are α-1,4-bonded to glucose residue of 1-menthyl-α-D-glucopyranoside.

EXAMPLES

Example 1
Production of Menthol Glycoside With Various Microorganism 50 mg of 1-menthol was added to 10 ml of 10 mM citric acidphosphoric acid buffer solution (pH7.0) containing 1M of maltose and then 50 mg of frozen dry bacteria of various kinds of microorganisms was added thereunto for subsequent shaking at 180 rpm to cause reactions at 30° C. for 24 hours. After the reaction was finished existence of menthol glycoside was detected by thin layer chromatography (TLC). Results of the detection are shown on the following table 1.

TABLE 1

| Microorganisms | menthol glycosides |
| --- | --- |
| Xanthomonas campestris IFO 13551 | detected |
| Xanthomonas campestris WU9701 (FERM BP-6578) | detected |
| Xanthomonas phaseoli IFO 13553 | detected |
| Xanthomonas phaseoli IFO 13554 | detected |
| Xanthomonas pisi IFO 13556 | detected |
| Xanthomonas oryzae IFO 3312 | detected |
| Xanthomonas oryzae IFO 3995 | detected |
| Xanthomonas arboricola IFO 3780 | detected |
| Xanthomonas arboricola IFO 13557 | detected |
| Xanthomonas cucurbitae IFO 13552 | detected |
| Xanthomonas citri IFO 3781 | detected |
| Xanthomonas citri IFO 3829 | detected |
| Xanthomonas citri IFO 12213 | detected |
| Stenotrophomonas maltophilia D1 (FERM BP-6579) | detected |
| Stenotrophomonas maltophilia JCM 1984 | detected |
| Stenotrophomonas maltophilia JCM 1987 | detected |
| Arthrobacter viscosus IFO 13497 | detected |
| Pseudomonas aeruginosa IFO 14160 | not detected |
| Pseudomonas putida IFO 14164 | not detected |
| Agrobacterium rhizogens IFO 15202 | not detected |
| Agrobacterium radiobacter IFO 13532 | not detected |
| Flateuria aurantia IFO 3245 | not detected |
| Aureobasidium pullulans IFO 7757 | not detected |
| Enterobacter aerogenes JCM 1235 | not detected |
| Asperigillus niger ATCC 20611 | not detected |
| Asperigillus niger var usamil JCM 2262 | not detected |
| Asperigillus terreus IFO 6123 | not detected |
| Penicillium chrysogennm IFO 4626 | not detected |
| Penicillium glabrum IFO 7919 | not detected |
| Penicillium commune IFO 5763 | not detected |
| Trichoderma reesei IFO 31329 | not detected |
| Rhizopus microsporus var oligosporus IFO 8631 | not detected |
| Saccharomyces cerevisiae JCM 7255 | detected |
| Kluyveromyces fragilis (Sigma frozen dry bacterium) | not detected |
| Candida uiillis (Sigma frozen dry bacterium) | not detected |

IFO: Institute of Fermentation Research (Foundation)
JCM: Institute of Physical and Chemical Research (Foundation)
ATCC: American Type Culture Collection
FERM: National Institute of Bioscience and Human-Technology in Agency of Industrial Science and Technology in Japan The above Table 1 shows that microorganisms classified into Xanthomonas species, Stenotrophomonas species, Arthrobacter species and Saccharomyces species have the capability of producing menthol glycoside from menthol.

The thin layer chromatography (TLC) was carried out by use of silica gel plates for development at a ratio of benzene to methanol of 3:1, before an anisaldehyde-sulfuric acid is sprayed for carrying out a heat treatment at 160° C. for one minute in order to detect menthol glycoside. Under those conditions, menthol glycoside can be detected at Rf value in the range of about 0.6 to about 0.7.

Example 2
Confirmation of Reaction Product

In order to confirm the reaction products, menthol glycoside was prepared in the following method. Xanthomonas campestris WU9701 (FERM BP-6578) was cultivated on mediums shown on the following Table 2 at 30° C. for 24 hours so that bacteria were separated from cultivation supernatant by a centrifugal separator under conditions of 10000 g and 30 min. The obtained bacteria were cleaned with 10 mM citric acid—phosphoric acid buffer solution (pH7.0) for carrying out subsequent freezing and drying processes to prepare frozen and dry bacteria. Other mediums than Table 2 may be available to cultivate bacteria.

TABLE 2

| Composition of Medium | |
| --- | --- |
| maltose | 50 g |
| yeast extract | 2 g |
| peptone | 10 g |
| MgSO$_4$-7H$_2$O | 1 g |
| distilled water | 1 liter |
| pH 7.0 | |

50 mg of 1-menthol was added to 10 ml of 10mM citric acidphosphoric acid buffer solution (pH7.0) containing 1M of maltose and then 50 mg of the above frozen dry bacteria was added thereunto for subsequent shaking at 180 rpm to cause a reaction at 30° C. for 24 hours. Reaction solution was then extracted with ethyl acetate for removal of a solvent of the extract before and subsequent dissolution into a mixture solvent of n-butanol/2-propanol/water (10:5:4) for supplying the same onto a silica gel column (Wako gel C200, φ25×400 mm). An elution was carried out with the same solvent to fractionate and collect an elute. Composition of the elute were confirmed by the thin layer chromatography (TLC) to select fractions on which the reaction products could be confirmed so that solvents of the selected fractions were removed before the reaction products were cleaned with hexane and then dried. It was confirmed that 31.3 mg of the product shows a single spot on the thin layer chromatography (TLC). Subsequently, the product was subjected to $^{13}$C-NMR analysis. Results of the analysis are organic-chemically synthesized in the method as disclosed in 1979, Agric. Biol. Chem. Vol. 43, p. 307, to confirm the correspondence with the already confirmed analysis results of standard product of 1-menthyl-α-D-glucopyranoside. FIG. 1 is a diagram illustrative of spectrum of $^{13}$C-NMR analysis to 1-menthyl-α-D-glucopyranoside obtained by the method in accordance with the present invention.

Example 3
Determination of the Reaction Product

In Example 1, there were confirmed relatively large spots of the products on the thin layer chromatography (TLC) for seven strains, for example, Xanthomonas campestris WU9701 (FRM BP-6578), Xanthomonas campestris IFO 13551, Xanthomonas phaseoli 13554, Xanthomonas pisi IFO 13556, Stenotrophomonas maltophilia D1 (FERM BP-6579), Stenotrophomonas maltophilia JCM 1984, Stenotrophomonas maltophilia JCM 1987. An amount of menthol glycoside produced in the reaction solution was determinated by the HPLC in the method as disclosed in 1996, Biosci. Biotech. Biochem. 60(11) pp. 1914–1915. It was confirmed that 15.9–35.8 mg of menthol glycoside was produced. The yield was about 16–35% in molar conversion. Results of the determinations are shown on the following Table 3.

TABLE 3

| Microorganisms | amount of produced menthol glycoside (mg) |
| --- | --- |
| Xanthomonas campestris WU9701 (FERM BP-6578) | 35.8 |
| Xanthomonas campestris IFO 13551 | 29.4 |
| Xanthomonas phaseoli IFO 13554 | 27.2 |
| Xanthomonas pisi IFO 13556 | 27.6 |
| Stenotrophomonas maltophilia D1 (FERM BP-6579) | 26.6 |
| Stenotrophomonas maltophilia JCM 1984 | 15.9 |
| Stenotrophomonas maltophilia JCM 1987 | 31.2 |

Example 4
Influence of Reaction pH to Production Amount of Menthol Glycoside In order to investigate influence of reaction pH on the production amount of menthol glycoside, 50 mg of 1-menthol was added on 10 ml of 10 mM buffer solution phosphoric acid—citric acid buffer solution or boric acid—NaOH buffer solution) which has a predetermined pH value and contains 1M of maltose and then 50 mg of frozen dry strain of *Xanthomonas campestris* WU9701 (FERM BP-6578) was added thereunto for subsequent reciprocal shaking at 180 rpm to cause reactions at 30° C. for 24 hours. After the reaction was finished, menthol glycoside was determined by HPLC.

Figure 2:
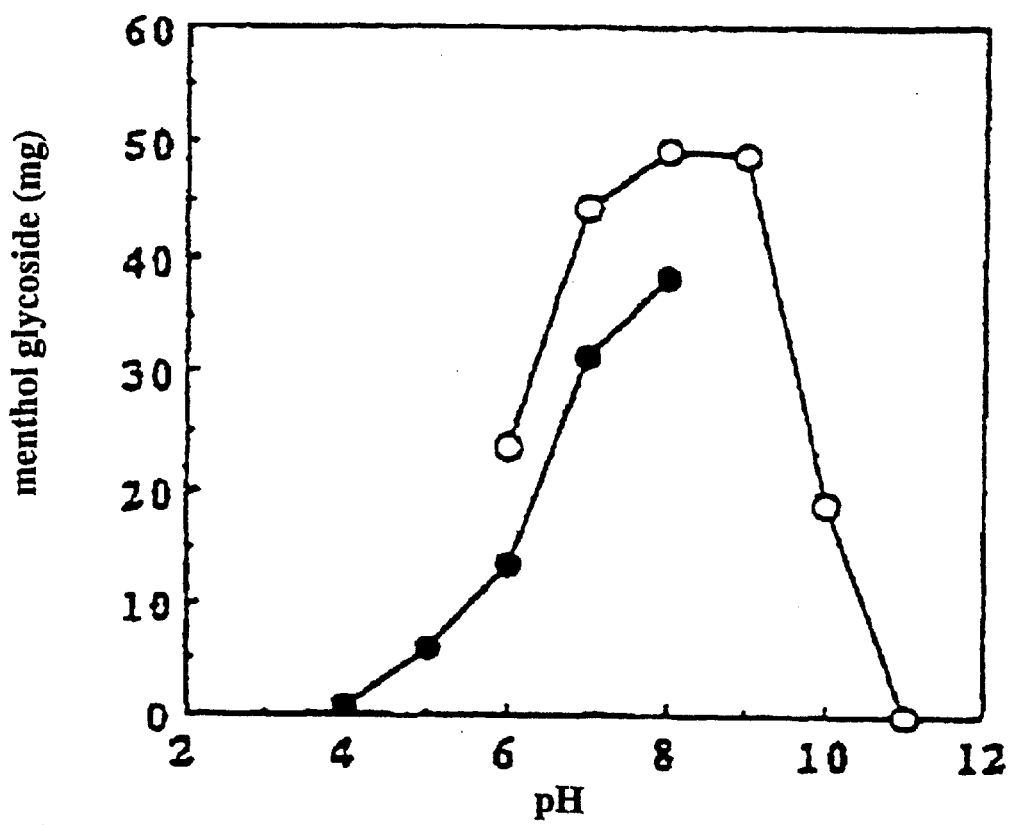
FIG. 2 is a diagram illustrative of an influence of reaction pH to production amount of menthol glycoside in Example 4.

FIG. 2 is a diagram illustrative of an influence of reaction pH on production amount of menthol glycoside in Example 4. Menthol glycoside was produced in the range of pH from 4 to 10. The production amount of menthol glycoside was maximized at pH 8. At this time, 49.3 mg of menthol glycoside was obtained. The yield was 44% in molar conversion.

Example 5
Influence of Reaction pH on Production Amount of Menthol Glycoside Instead of 50mg of frozen dry strain of *Xanthomonas campestris* WU9701 (FEP P-6578), *Stenotrophomonas maltophilia* D1 (FERM BP-6579) was used. Determination of the, produced menthol glycoside was made in the same manners as in Example 4.

Figure 3:
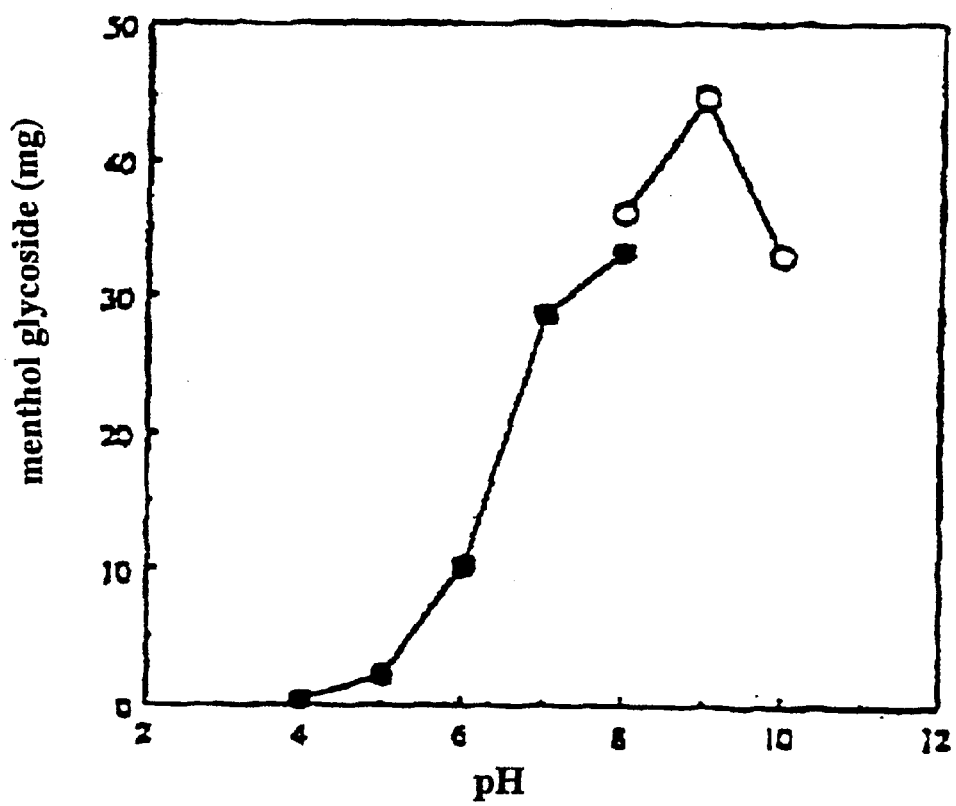
FIG. 3 is a diagram illustrative of an influence of reaction pH to production amount of menthol glycoside in Example 5.

FIG. 3 is a diagram illustrative of an influence of reaction pH on production amount of menthol glycoside in Example 5. Menthol glycoside was produced in the range of pH from 4 to 10. The production amount of menthol glycoside was maximized at pH 9. At this time, 45 mg of menthol glycoside was obtained. The yield was 44% in molar conversion.

Example 6
Influence of Reaction Temperature on Production Amount of Menthol Glycoside In order to investigate influence of reaction temperature on the production amount of menthol glycoside, 50 mg or 100 mg of 1-menthol was added to 10 ml of 10 mM boric acid—NaOH buffer solution with pH 8 containing 1M of maltose and then 50 mg of frozen dry strain of *Xanthomonas campestris* WU9701 (FERM BP-6578) was added thereunto for subsequent reciprocal shaking at 180 rpm to cause reactions at a predetermined temperature for 24 hours. After the reaction was finished, menthol glycoside was determined by HPLC.

Figure 4:
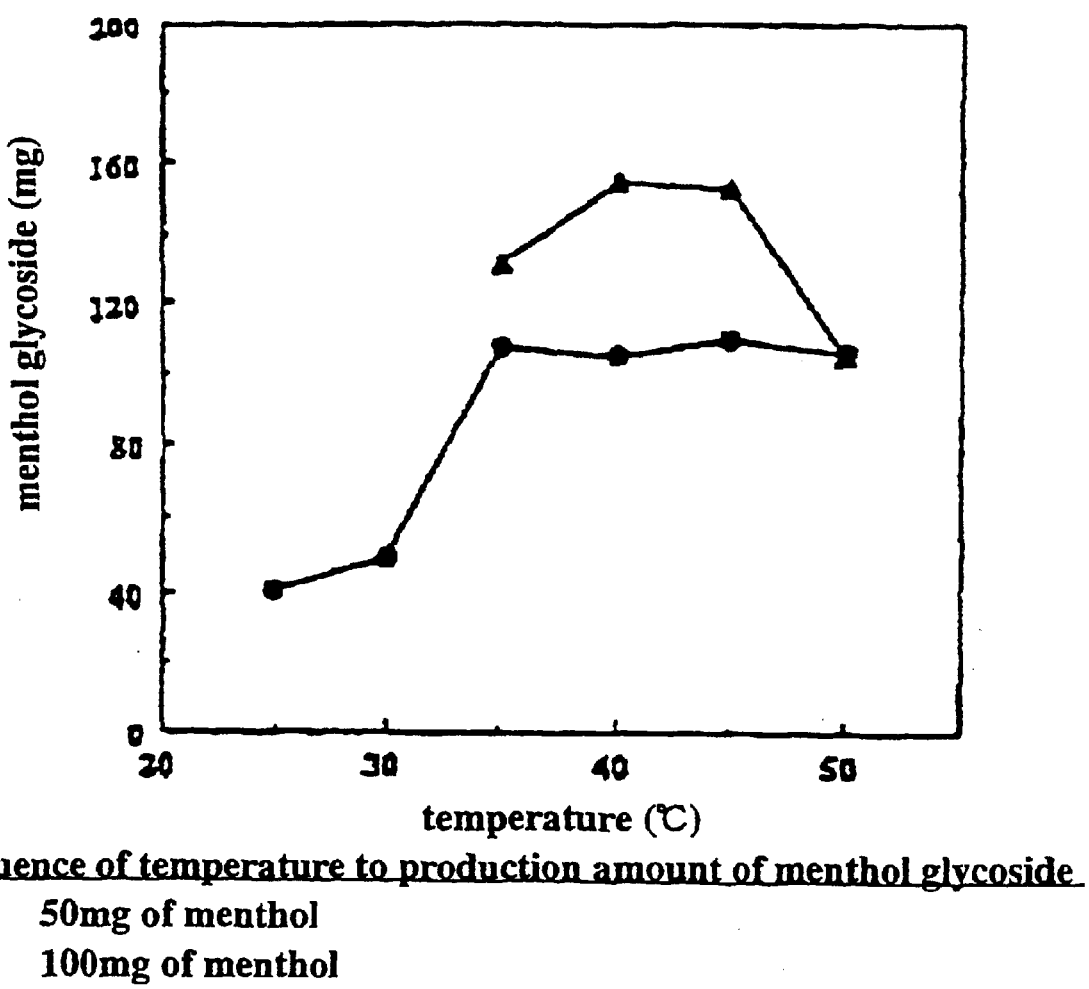
FIG. 4 is a diagram illustrative of an influence of reaction temperature to production amount of menthol glycoside in Example 6.

FIG. 4 is a diagram illustrative of an influence of reaction temperature on production amount of menthol glycoside in Example 6. Menthol glycoside was produced in the range of temperature from 25–50° C. When 50 mg of 1-menthol was added, the yield was 100% at a temperature of not less than 35° C. All of added menthol were made into menthol glycoside. When 100 mg of 1-menthol was added, the production amount of menthol glycoside was maximized at 40° C. At this time, 154.7 mg of menthol glycoside was obtained. The yield was 75.8% in molar conversion.

Example 7
Influence of Reaction Temperature on Production Amount of Menthol Glycoside Instead of 50 mg of frozen dry strain of *Xanthomonas campestris* WU9701 (FERM BP-6578), *Stenotrophomonas maltophilia* D1 (FERM BP-6579) was used. Also instead of boric acid—NaOH buffer solution with pH 8, citric acid—phosphoric acid buffer solution with pH 7 was used. Determination of the produced menthol glycoside was made in the same manners as in Example 6.

Figure 5:
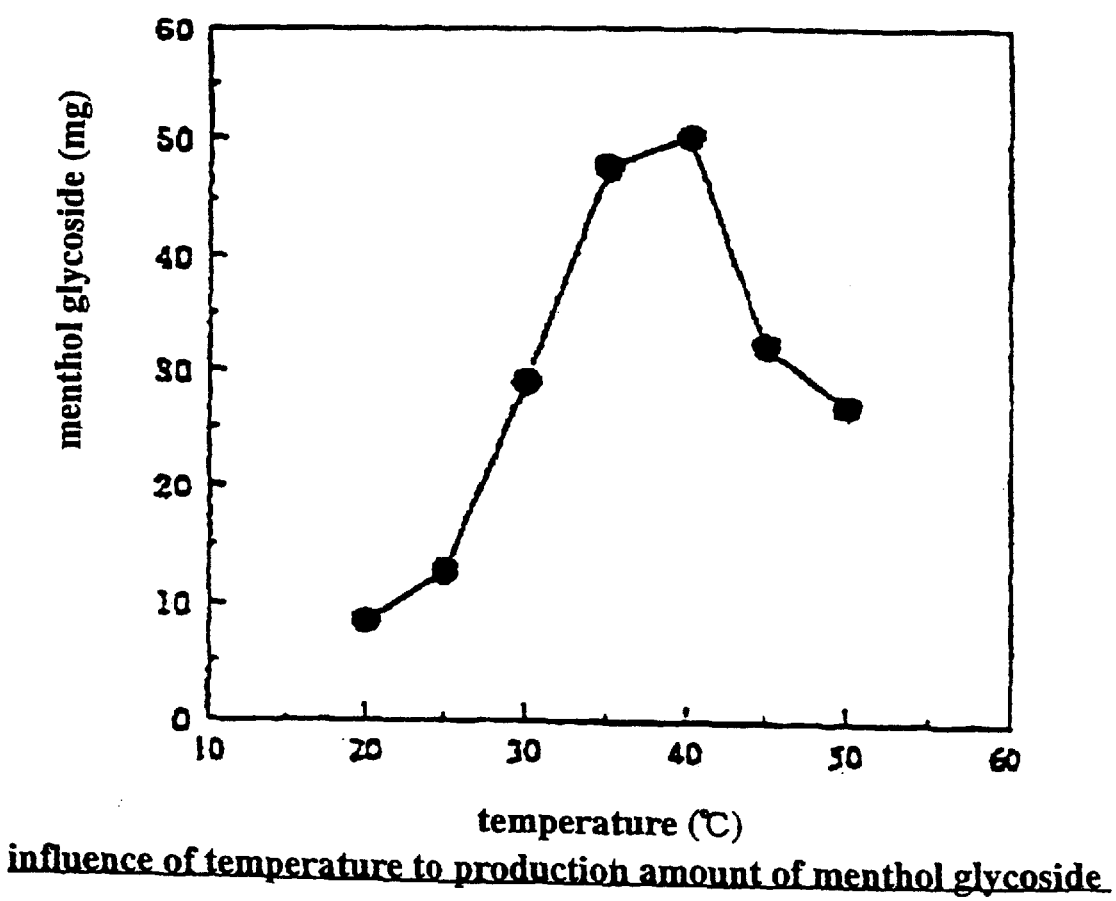
FIG. 5 is a diagram illustrative of an influence of reaction temperature to production amount of menthol glycoside in Example 7.

FIG. 5 is a diagram illustrative of an influence of reaction temperature on production amount of menthol glycoside in Example 7. Menthol glycoside was produced at a temperature in the range of 20–50° C. The temperature range of 35–40° C. was optimum. At a reaction temperature of 40° C., 50 mg of menthol glycoside was produced. The yield was 49% in molar conversion.

Example 8
Influence of Maltose Concentration on Production Amount of Menthol Glycoside In order on investigate influence of reaction temperature to the production amount of menthol glycoside, 100 mg of 1-menthol was added to 10 ml of 10 mM boric acid: NaOH buffer solution with pH 8 containing a predetermined amount of maltose and then 50 mg of frozen dry strain of *Xanthomonas campestris* WU9701 (FERM BP-6578) was added thereunto for subsequent reciprocal shaking at 180 rpm to cause reactions at 40° C. for 24 hours. After the reaction was finished, menthol glycoside was determined by HPLC.

Figure 6:
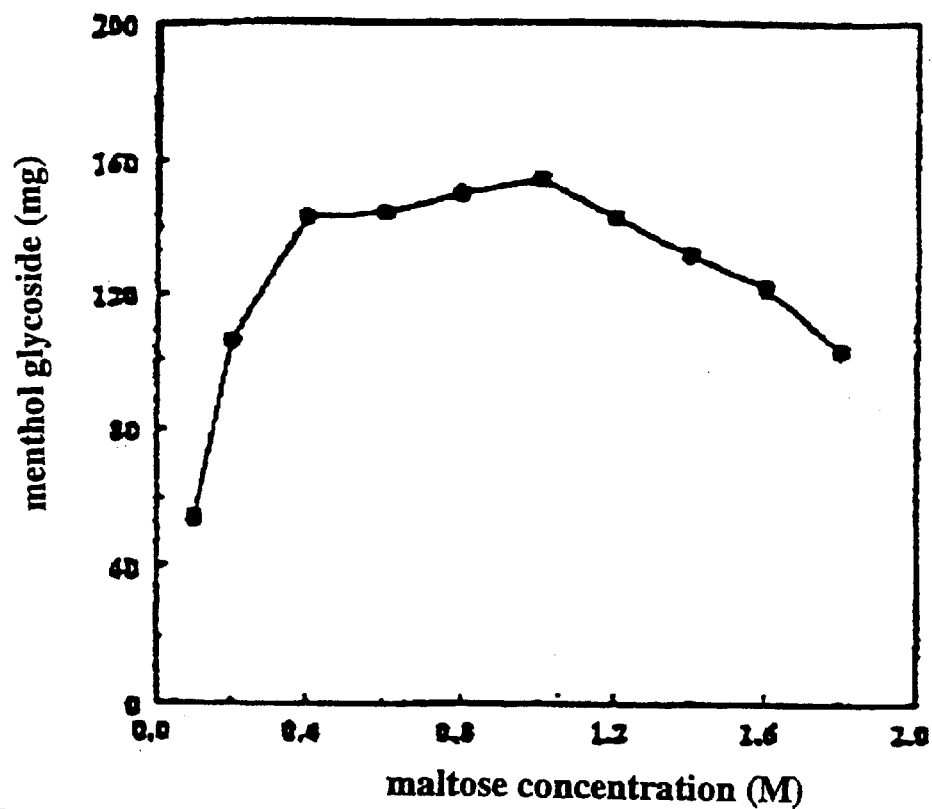
FIG. 6 is a diagram illustrative of an influence of maltose concentration to production amount of menthol glycoside in Example 8.

FIG. 6 is a diagram illustrative of an influence of maltose concentration on production amount of menthol glycoside in Example 8. Menthol glycoside was produced in the range of maltose concentration from 0.1M to 1.8M. Not less than 140 mg of menthol glycoside was produced in the range of maltose concentration from 0.4M to 1.2M. The production amount of menthol glycoside was maximized at a maltose concentration of 1M. At this time, 154 mg of menthol glycoside was obtained. The yield was 75% in molar conversion.

Example 9
Influence of Maltose Concentration on Production Amount of Menthol Glycoside Instead of 50 mg of frozen dry strain of *Xanthomonas campestris* WU9701 (FERM BP-6578), *Stenotrophomonas maltophilia* D1 (FERM BP-6579) was used. Also instead of boric acid—NaOH buffer solution with pH 8, citric acid—phosphoric acid buffer solution with pH 7 was used. Determination of the produced menthol glycoside was made in the same manners as in Example 8.

Figure 7:
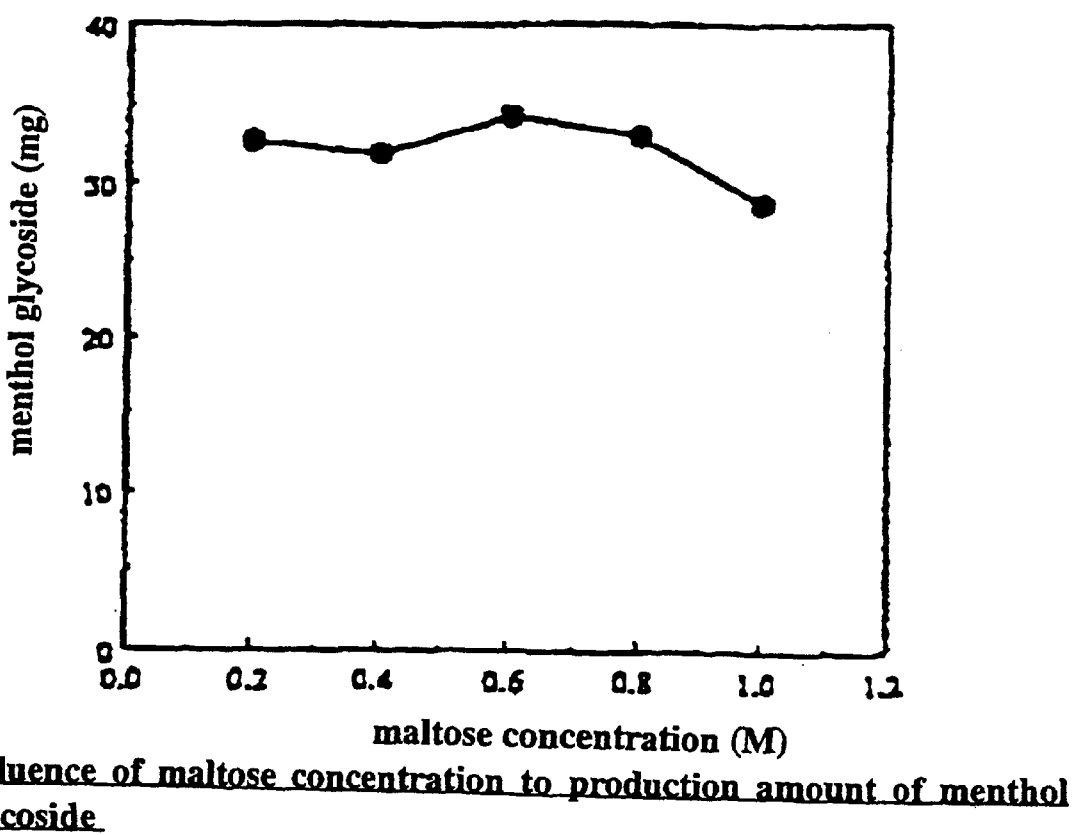
FIG. 7 is a diagram illustrative of an influence of maltose concentration to production amount of menthol glycoside in Example 9.

FIG. 7 is a diagram illustrative of an influence of maltose concentration on production amount of menthol glycoside in Example 9. Menthol glycoside was produced in the range of maltose concentration from 0.2M to 1.0M. In this range, the yield almost remains unchanged. 29–34 mg of menthol glycoside was produced.

Example 10
Influence of Amount of Menthol on Production Amount of Menthol Glycoside In order to investigate influence of amount of menthol on the production amount of menthol glycoside, a predetermined amount of 1-menthol was added to 10 ml of 10 mM boric acid—NaOH buffer solution with pH 8 containing 1M of maltose and then 50 mg of frozen dry strain of *Xanthomonas campestris* WU9701 (FERM BP-6578) was added thereunto for subsequent reciprocal shaking at 180 rpm to cause reactions at 40° C. for 24 hours. After the reaction was finished, menthol glycoside was determined by HPLC.

Figure 8:
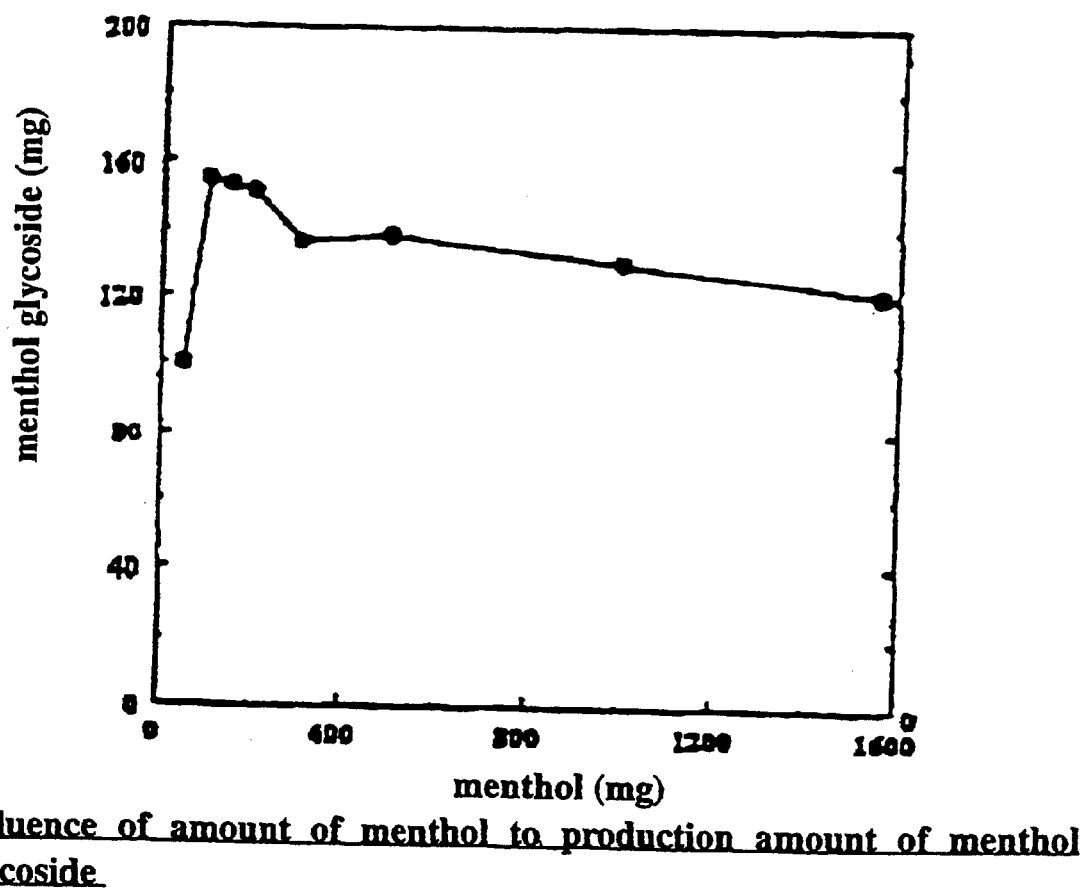
FIG. 8 is a diagram illustrative of an influence of amount of menthol to production amount of menthol glycoside in Example 10.

FIG. 8 is a diagram illustrative of an influence of amount of menthol on production amount of menthol glycoside in Example 10. Menthol glycoside was produced in the range of menthol amount from 50 mg to 1563 mg. The production amount of menthol glycoside was maximized at a menthol amount of 100 mg. No further increase in production amount of menthol glycoside was confirmed even more than 100 mg of menthol was added When 50 mg of menthol was added, the yield was 100%. When the amount of menthol to be added was increased from 50 mg, the yield was gradually decreased.

Example 11
Influence of Reaction Time on Production Amount of Menthol Glycoside In order to investigate influence of reaction time on the production amount of menthol glycoside, 100 mg of 1-menthol was added to 10 ml of 10 mM boric acid—NaOH buffer solution with pH 8 containing 1M of maltose and then 50 mg of frozen dry strain of *Xanthomonas campestris* WU9701 (FERM BP-6578) was added thereunto for subsequent reciprocal shaking at 180 rpm to cause reactions at 40° C. for 0.5–72 hours. Over reaction times of 0.5–72 hours, menthol glycoside was determined by HPLC.

Figure 9:
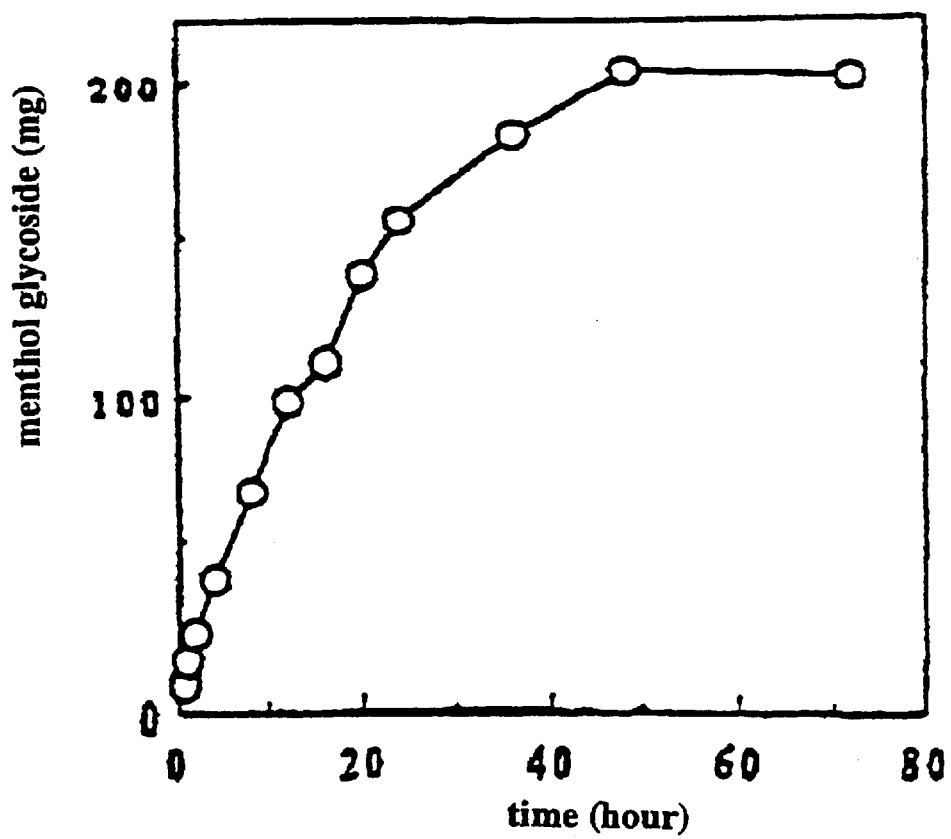
FIG. 9 is a diagram illustrative of an influence of reaction time to production amount of menthol glycoside in Example 11.

FIG. 9 is a diagram illustrative of an influence of reaction time to production amount of menthol glycoside in Example 11. An initial production of menthol glycoside appeared at 0.5 hour after the reaction was started. The production amount of menthol glycoside was increased over time. At 48 hours after the reaction was started, all of the menthol as added was made into menthol glycoside.

Comparative Example
Production of Menthol Glycoside with α-glucosidase 50 mg of menthol was added to 10 ml of 10 mM citric acid-phosphoric acid buffer solution (pH7.0) containing 1M of maltose and then 20 units or 100 units of α-glucosidase derived from yeast and commercially available from Biozyme laboratory Limited in United Kingdom was added thereunto for subsequent reactions at 30° C. for 24 hours to form menthol glycoside. α-glucosidase was standardized by the necessary amount of enzyme for hydrolyzing 1 micro-M of maltose at 37° C. for one minute. After the reaction was finished, existence of menthol glycoside was detected by thin layer chromatography (TLC). Results of the detection are shown on the following table 4.

TABLE 4

| α-glucosidase | amount of produced menthol glycoside (yield in molar conversion) |
| --- | --- |
| 20 units | 4.8 mg (4.7%) |
| 100 units | 1.9 mg (1.9%) |

*yield in molar conversion = number of moles of produced menthol glycoside/number of moles of used menthol When 20 units of α-glucosidase was added, 4.8 mg of menthol glycoside was produced. The yield was low at 4.7% in molar conversion. Even if the amount of enzyme was increased by five times so that 100 units of α-glucosidase was added, the amount of produced menthol glycoside was decreased.

Example 12
Production of Menthol Glycoside With Crude Enzyme Prepared From Microorganisms Bacteria

*Xanthomonas campestris* WU9701 (FERM BP-6578) was cultivated on mediums shown on the above Table 2 at 30° C. for 24 hours so that bacteria were separated from 30 ml of cultivation supernatant by a centrifugal separator under conditions of 4° C., 10000 g and 30 min. The obtained bacteria were cleaned two times with 10 mM citric acid—phosphoric acid buffer solution (pH7.0) and then suspended with 10 ml of 10 mM citric acid—phosphoric acid buffer solution for carrying out subsequent ultrasonic wave treatment at 20 kHz and 200 W for two minutes and this treatment was repeated ten times at one minute intervals to crush cells of the bacteria. The obtained crushed bacteria solution was separated into supernatant and residue so that the supernatant was used as the crude enzyme to produce menthol glycoside. 1M of maltose and 50 mg of menthol were added to about 10 ml of the crude enzyme solution to cause a reaction at 40° C. for 24 hours. The obtained menthol glycoside was determined by HPLC.

89.3 mg of menthol glycoside was produced. The yield was 88.2% in molar conversion. Results of the detection are shown on the following table 5.

TABLE 5

| amount of produced menthol glycoside | yield in molar conversion |
| --- | --- |
| 89.3 mg | 88.2% |

In accordance with the present invention, even if enzyme obtained from microorganisms capable of producing menthol glycoside from menthol is used, then menthol glycoside could be produced at high yield. In consideration of the fact that the yield of producing menthol glycoside with the enzyme obtained from the microorganisms is much higher than the yield of producing menthol glycoside with α-glucosidase, it is presumable that the enzyme obtained from the microorganisms is quite different in enzymologic properties such as classification and substrate specificity from α-glucosidase.

Example 13
Influence of Kinds of Sugar Donor to Menthol Glycoside Synthesis

Crude enzyme was prepared from *Xanthomonas campestris* WU9701 (FERM BP-6578) in the same manner as in Example 12. Thereafter, 1 g of a predetermined kind of sugar and 50 mg of menthol were added to 10 ml of the crude enzyme solution to cause a reaction at 30° C. for 24 hours. The obtained menthol glycoside was determined by HPLC.

If maltose, soluble starch or sucrose was used, then menthol glycoside was produced. If glucose was used, then no menthol glycoside was produced. Results of the detection are shown on the following table 6.

TABLE 6

|  | Menthol glycoside | | |
|---|---|---|---|
|  | amount (mg) | yield (%) | relative ratio (%) |
| maltose | 69.7 | 68.3 | 100.0 |
| soluble starch | 8.4 | 8.2 | 12.0 |
| sucrose | 1.4 | 1.4 | 2.0 |
| glucose | 0.0 | 0.0 | 0.0 |

*relative ratio is calculated with reference to the production amount of menthol glycoside obtained by the reaction using maltose.
*The yield is presented by percentage in molar conversion.

Example 14
Preparation of Chewing Gum

Chewing gum was prepared in the following prescriptions using menthol glycoside obtained in Example 6.

| Gum base | 20.0% |
|---|---|
| Sugar | 55.0% |
| Corn syrup | 14.0% |
| Glucose | 10.4% |
| Essence | 0.1% |
| Menthol glycoside | 0.5% |

Example 15
Preparation of Tablet Type Confectionery

Tablet type confectionery was prepared in the following prescriptions using menthol glycoside obtained in Example 6.

| Sugar | 75.0% |
|---|---|
| Lactose | 19.5% |
| Purified water | 4.3% |
| Essence | 0.5% |
| Glycerin fatty acid ester | 0.2% |
| Menthol glycoside | 0.5% |

Example 16
Preparation of Ice Cream

Ice cream was prepared in the following prescriptions using menthol glycoside obtained in Example 6.

| Cream (45% fat) | 25.0% |
|---|---|
| Milk (3.7% fat) | 35.0% |
| Skimmilk | 24.3% |
| Sugar | 10.2% |
| Corn syrup | 4.7% |
| Stabilizer | 0.3% |
| Menthol glycoside | 0.5% |

Example 17
Preparation of Chocolate

Chocolate was prepared in the following prescriptions using menthol glycoside obtained in Example 6.

| Cacao mass | 15.0% |
|---|---|
| Whole milk powder | 25.0% |
| Cocoa butter | 18.0% |
| Sugar | 41.0% |
| Emulsifier | 0.3% |
| Essence | 0.1% |
| Menthol glycoside | 0.6% |

Example 18
Preparation of Soft Drink

Soft drink was prepared in the following prescriptions using menthol glycoside obtained in Example 6.

| Fructose glucose liquid sugar | 5.0% |
|---|---|
| Sugar | 4.0% |
| Sourness | 1.2% |
| Essence | 0.3% |
| Purified water | 89.0% |
| Menthol glycoside | 0.5% |

Example 19
Preparation of Toothpaste

Toothpaste was prepared in the following prescriptions using menthol glycoside obtained in Example 6.

| Lauryl sodium sulfate | 1.0% |
|---|---|
| Aluminum hydroxide | 35.0% |
| Silicic anhydride | 15.0% |
| Sodium saccharide | 0.2% |
| Sorbitol | 0.5% |
| Essence | 0.7% |
| Purified water | 47.1% |
| Menthol glycoside | 0.5% |

Example 20
Preparation of Mouth-Washing Liquid

Mouth-washing liquid was prepared in the following prescriptions using menthol glycoside obtained in Example 6.

| Lauryl sodium sulfate | 1.5% |
|---|---|
| Glycerin | 10.0% |
| Ethanol | 5.0% |
| Sodium saccharide | 0.2% |
| Essence | 0.5% |
| Purified water | 82.3% |
| Menthol glycoside | 0.5% |

Example 21
Preparation of lotion

Lotion was prepared in the following prescriptions using menthol glycoside obtained in Example 6.

| Ethanol | 30.0% |
|---|---|
| 1-menthol | 0.1% |
| Emulsifier | 0.5% |
| Purified water | 68.9% |
| Menthol glycoside | 0.5% |

Whereas modifications of the present invention will be apparent to a person having ordinary skill in the art, to which the invention pertains, it is to be understood that examples as shown and described by way of illustrations are by no means intended to be considered in a limiting sense. Accordingly, it is intended to cover by the following claims all modifications which fall within the spirit and scope of the present invention.

What is claimed is:

1. A method of producing 1-menthyl-α-D-glucopyranoside, which comprises adding bacteria capable of producing 1-menthol glycoside from 1-menthol to sugars and 1-menthol in a reaction medium and separating the thus produced 1-menthyl-α-D-glucopyranoside from the reaction medium, wherein said bacteria is at least one selected from the group consisting of *Xanthomonas campestris, Xanthomonas phaseoli, Xanthomonas pisi, Xanthomonas oryzae, Xanthomonas cucurbitae, Xanthomonas citri* and *Stenotrophomonas maltophilia*.

2. A method of producing 1-menthyl-α-D-glucopyranoside, which comprises adding a crude enzyme prepared from bacteria capable of producing 1-menthol glycoside from 1-menthol, to sugars and 1-menthol, in a reaction medium, and separating the thus-produced 1-menthyl-α-D-glucopyranoside from the reaction medium, wherein said bacteria is at least one selected from the group consisting of *Xanthomonas campestris, Xanthomonas phaseoli, Xanthomonas pisi, Xanthomonas oryzae, Xanthomonas cucurbitae, Xanthomonas citri* and *Stenotrophomonas maltophilia*.

* * * * *